US008596326B2

(12) United States Patent
Loy (10) Patent No.: US 8,596,326 B2
(45) Date of Patent: Dec. 3, 2013

(54) DEVICE FOR MAINTAINING STERILE INTEGRITY OF CONNECTED FLUID PATHWAYS

(75) Inventor: Larry H. Loy, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 214 days.

(21) Appl. No.: 13/262,269

(22) PCT Filed: Apr. 7, 2010

(86) PCT No.: PCT/US2010/030191
§ 371 (c)(1),
(2), (4) Date: Dec. 16, 2011

(87) PCT Pub. No.: WO2010/118099
PCT Pub. Date: Oct. 14, 2010

(65) Prior Publication Data
US 2012/0073763 A1    Mar. 29, 2012

Related U.S. Application Data (60) Provisional application No. 61/168,286, filed on Apr. 10, 2009.

(51) Int. Cl.
*A61M 39/18* (2006.01)
*B32B 38/10* (2006.01)

(52) U.S. Cl.
USPC ........... 156/750; 156/247; 156/378; 156/503; 156/714; 29/268; 604/905

(58) Field of Classification Search
USPC .............. 156/247, 304.2, 378, 503, 714, 718, 156/750; 29/268, 423, 721; 604/905
See application file for complete search history.

(56) References Cited

U.S. PATENT DOCUMENTS

| | | | |
|---|---|---|---|
| 3,909,910 A * | 10/1975 | Rowe et al. | .................... 29/423 |
| 6,397,842 B1 | 6/2002 | Lee | |
| 2004/0127863 A1 | 7/2004 | Bubb et al. | |
| 2005/0075600 A1 | 4/2005 | Nelson et al. | |
| 2006/0161135 A1 | 7/2006 | VanDerWoude | |

* cited by examiner

*Primary Examiner* — Michael Tolin
(74) *Attorney, Agent, or Firm* — Womble Carlyle Sandridge & Rice, LLP (57) ABSTRACT

A device is provided for ensuring the sterile integrity of two separate fluid pathways during interconnection of the two pathways with a two-part connector assembly. The two-part connector assembly is of the type which comprises a male portion and a female portion, each portion initially having a port covered and protected by a peel-away strip. The device comprises a base assembly, a connector clamp assembly mounted to the base assembly and configured for securing the two-part connector assembly in position for interconnection of the male and female portions, and a strip withdrawal assembly mounted to the base assembly and configured for simultaneous withdrawal of the peel-away strips from the ports of the male and female portions.

11 Claims, 7 Drawing Sheets

DEVICE FOR MAINTAINING STERILE INTEGRITY OF CONNECTED FLUID PATHWAYS

CROSS-REFERENCE TO RELATED APPLICATIONS

This application is a national phase of International Application PCT/US10/030191, filed Apr. 7, 2010, which claims priority under 35 USC §119 to U.S. Provisional Application No. 61/168,286, filed Apr. 10, 2009, each of which is herein incorporated by reference in its entirety.

FIELD OF THE INVENTION

The invention generally relates to technical applications involving the transfer of fluids under sterile conditions, and, more particularly, to devices which ensure the sterile integrity of connectors of fluid pathways during the connection thereof.

BACKGROUND

Sanitary and sterile piping, and fluid transfer systems, are essential to many industries, particularly medical, pharmaceutical, biotechnology, etc. In transferring fluid products for further processing or storage, bulk fluid transfer pathways and connections must be established and maintained. These often involve the realignment or configuration of sanitary piping/tubing systems, which comprise multiple manual and automated valves, including the associated temperature and pressure transmitters, regulators, filters, steam traps, etc. Ensuring the required levels of sterility of the fluid transfer pathways in these systems is thus critical, and often problematic.

In more recent years, disposable specialized fluid transfer systems have been introduced which permit quick connections and disconnections of fluid transfer tubing or piping, most of which is formed of plastic. One such system for sterile processes employs a two-part connector known as the KLEENPAK™ HT Connector, available from Pall Corporation Life Sciences (see FIGS. 1A and 1B). This connector permits a dry connection to be made between two separate fluid pathways, while maintaining the sterile integrity of both. The connector consists of male and female portions, each portion having a vented peel-away strip that protects the port, or pathway opening, and maintains the sterility of the fluid pathways before the two portions are connected. The vented peel-away strips should be simultaneously removed immediately before the two connector portions are engaged to form a sealed, locked connection.

However, even with newer connection systems such as the KLEENPAK™ HT Connector, manual removal of the peel-away strips and positive engagement of the two connector portions is still required. The normally field-executed manual process provides an opportunity for operator variations, incomplete assembly of the male and female portions, sideways withdrawal of the vented strips, partial withdrawal of the vented strips, and incomplete insertion of the male portion into the female portion, all of which are detrimental to the operation of the connection assembly, and which can lead to the potential breach of sterile integrity. For example, if the vented strips are not simultaneously and evenly withdrawn from the male and female portions, there is the potential that the exposed, and potentially contaminated, outer surface of one of the vented strips may contact and contaminate the exposed port of the other connector portion. This possibility, and the potential harmful results which could follow, have led to careful scrutiny by various regulatory agencies.

What is needed, therefore, is a consistently repeatable and validated process which increases the likelihood of maintaining the required sterility.

Various features and aspects of the invention will become apparent upon review of the detailed description set forth below when taken in conjunction with the accompanying drawing figures, which are briefly described as follows.

SUMMARY OF THE INVENTION

The present invention is directed to a device for ensuring the sterile integrity of two separate fluid pathways during interconnection of the two pathways with a two-part connector assembly comprising male and female portions. The exemplary KLEENPAK™ HT Connector is supplied with a peel-away strip covering and protecting the port of each portion. One embodiment of the device of the present invention includes a base assembly, a connector clamp assembly mounted to the base assembly and configured for securing the two-part connector assembly in position for interconnection of the male and female portions, and a strip withdrawal assembly mounted to the base assembly and configured for simultaneous withdrawal of the peel-away strips from the ports of the male and female portions.

DETAILED DESCRIPTION

Certain exemplary embodiments of the present invention are described below and illustrated in the accompanying figures. The embodiments described are only for purposes of illustrating the present invention and should not be interpreted as limiting the scope of the invention, which, of course, is limited only by the claims below. Other embodiments of the invention, and certain modifications and improvements of the described embodiments, will occur to those skilled in the art, and all such alternate embodiments, modifications and improvements are within the scope of the present invention.

The present invention is directed to a device which provides for a sterile process connection to be affected, using a commercially available and disposable connector, in a manner that requires all operator variability to be eliminated for consistent and repeatable execution, and which addresses the problems described above. For field execution of the KLEENPAK™ HT Connector (the "Connector"), the present invention: (1) provides a high level of security and protection from damage for the relatively fragile connector because the device is a stable and robust holder; (2) ensures that the male and female portions are fully snapped together before actuation; i.e., they will not insert into the cradle of the device unless properly assembled; (3) ensures simultaneous straight line pull of both vented strips for field execution of the connector; (4) ensures full withdrawal of the vented strips (the ratchet assembly described herein prevents premature return of the withdrawal lever); and, (5) ensures that the final step in the connection process results in a fully engaged connector (complete insertion of the male portion into the female portion) by use of an engagement gauge.

Figure 1A:
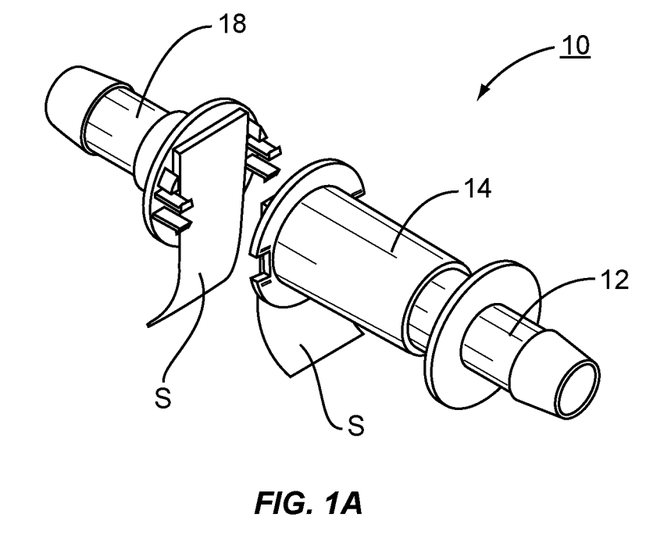
FIG. 1A is a schematic illustrating the configuration of the KLEENPAK™ HT Connector, including the male and female portions, and the vented peel-away strips.
Figure 1B:
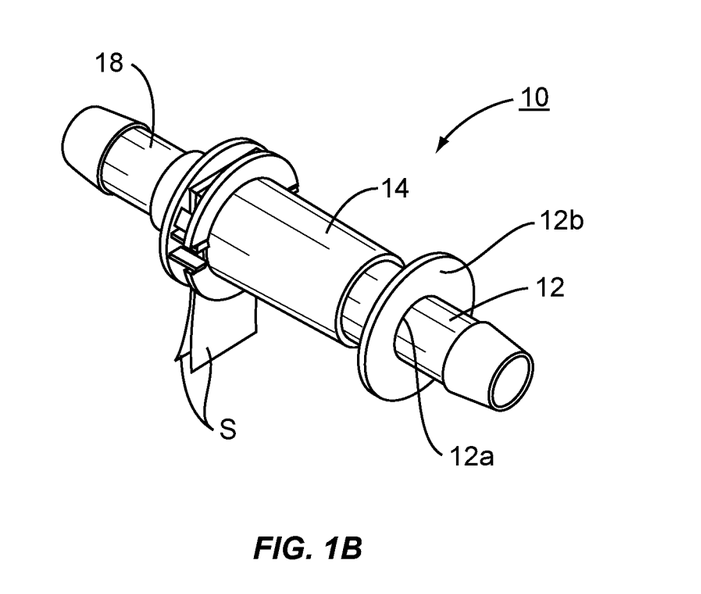
FIG. 1B illustrates the KLEENPAK™ HT Connector, with the male and female portions connected, but not fully engaged.

Turning now to FIGS. 1A and 1B, performing a field connection of a disposable connector 10, such as the KLEEN-PAK™ HT Connector, requires several steps: (1) removal of the protective end caps (not shown) from the male 12 and female 18 portions; (2) alignment of the male 12 and female 18 portions with the peel-away strips S facing each other, by pressing the two portions together until they snap tightly together (FIG. 1B); (3) withdrawal of the strips S simultaneously in a smooth, continuous motion; (4) rotation one partial turn of the thumb rest 12a on the male portion 12; and, (5) pushing of male portion 12 into the female portion 18 for full engagement. While this procedure takes only a few seconds, step (3) is critical and must be performed consistently to ensure sterile integrity each time that a field connection is performed. That is, manual withdrawal of the strips does not inherently guarantee successful execution of this step, as the pair of strips must be withdrawn from the male and female portions together completely and evenly, straight radially outward, and with no differential motion between the two strips. Further, the male and female portions must be fully engaged to ensure "crevice-free" functionality, and thus, sterility of the interconnected pathways.

Figure 2:
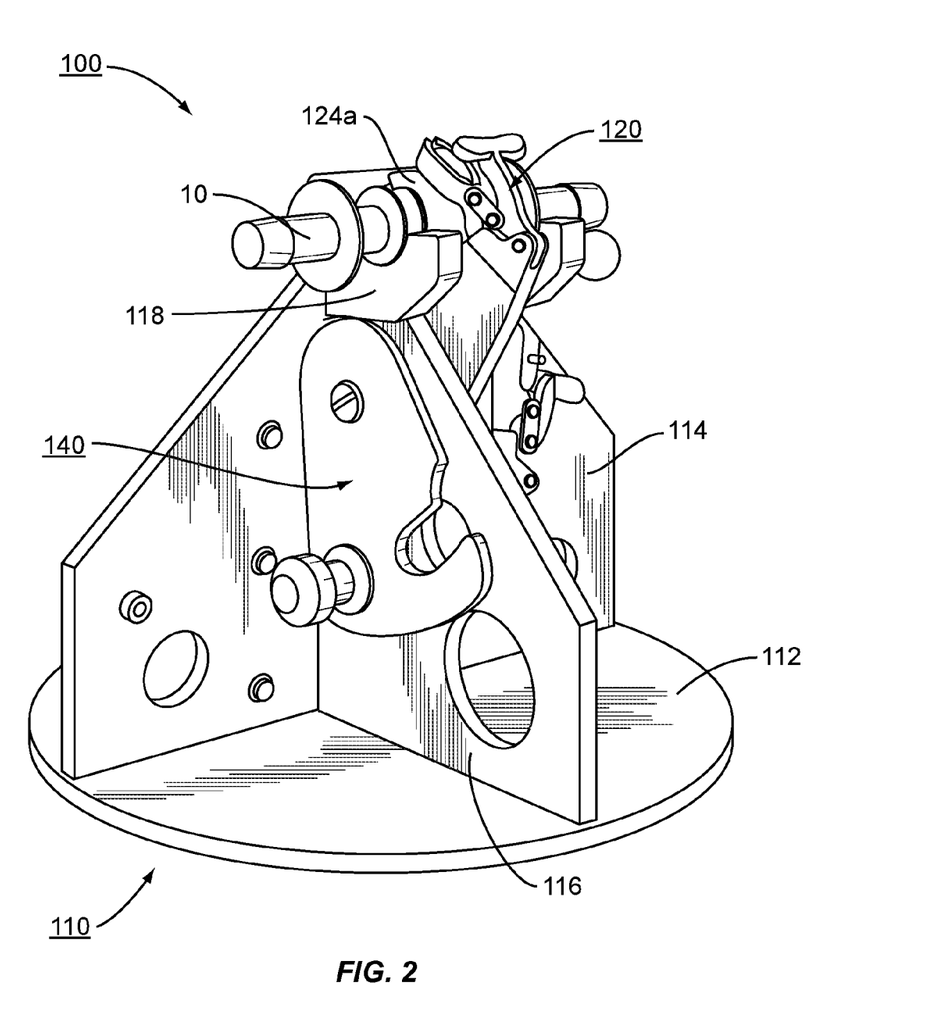
FIG. 2 is a left front perspective view of the device of the present invention.
Figure 3:
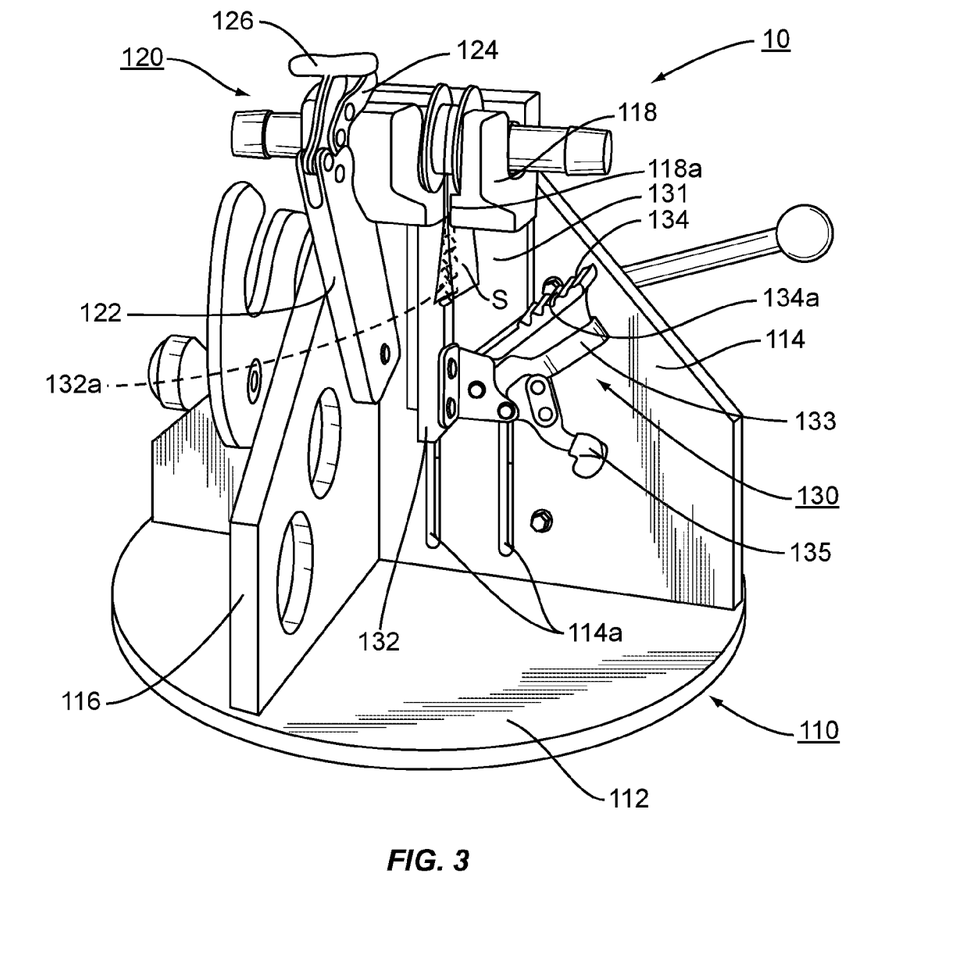
FIG. 3 is a right front perspective view of the device of the present invention.
Figure 7:
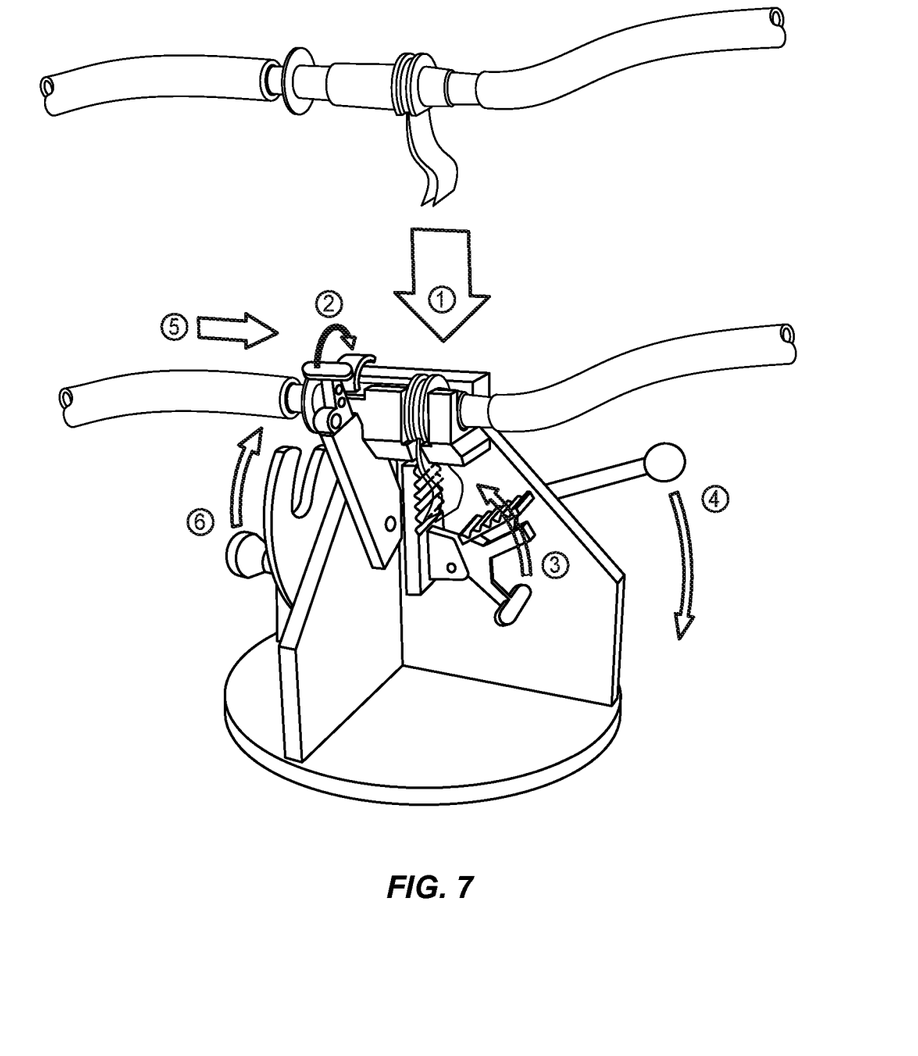
FIG. 7 is a schematic depicting the operation of the device of the present invention.

Referring now to FIGS. 2 through 5, one exemplary embodiment of the device, designated generally as 100, is shown. The device 100 comprises a base assembly 110, a connector clamp assembly 120, a strip removal assembly 130, and an optional engagement gauge 140. The base assembly 110 comprises a generally planar base 112, upstanding support walls 114, 116, and a cradle 118. As best shown in FIGS. 3 and 7, a slot 118a is formed through the cradle 118 through which the vented peel-away strips S will extend when the connector 10 is placed in the cradle 118. The connector clamp assembly 120 is mounted on one wall 116 and comprises a mounting arm 122 and toggle clamp 124 mechanism, the toggle clamp mechanism 124 being pivotally connected to the mounting arm 122. The mounting arm 122 may be mounted on the wall 116 by any conventional means of attachment, including fasteners, adhesives, etc. As will be appreciated by those skilled in the art, the components of the device 100 described herein may be formed from a variety of materials that sufficiently provide the required functional characteristics of the device 100. As shown in FIGS. 3 and 7, the toggle clamp 124 comprises a positive locking mechanism 126, which ensures that the clamp 124 remains in a closed, locked position with the arcuate end 124a (FIG. 2) of the clamp 124 against the connector 10 barrel (the larger diameter section of the connector) once the positive locking mechanism 126 is pivoted inwardly toward the connector 100. Those skilled in the art will appreciate that there are a number of mechanical assembly combinations which may form suitable pivotal locking mechanisms.

As shown in FIGS. 3, 6, 8, and 10, a strip removal assembly 130 is slidably mounted on the other wall 114 in vertical elongate slots 114a. The strip removal assembly 130 includes a slidable front mounting plate 131 to which a first clamping portion 132 is affixed. Serrated teeth 132a are formed on the face of the first clamping portion 132. A second clamping portion 134 is pivotally connected to the first clamping portion 132 for gripping engagement therewith. The second clamp portion 134 portion also has serrated teeth 134a, and a positive locking mechanism 133, which ensures that the second clamp 134 remains in a closed locked position so that the serrated teeth 134a of the second clamp portion 134 positively engage the serrated teeth 132a of the first clamp portion 132 when the positive locking mechanism 133 is pivoted upwardly and inwardly. In the closed, locked position, the positive locking mechanism 133 causes the serrated teeth 132a, 134a to firmly grip the pair of vented peel-away strips S.

Figure 4:
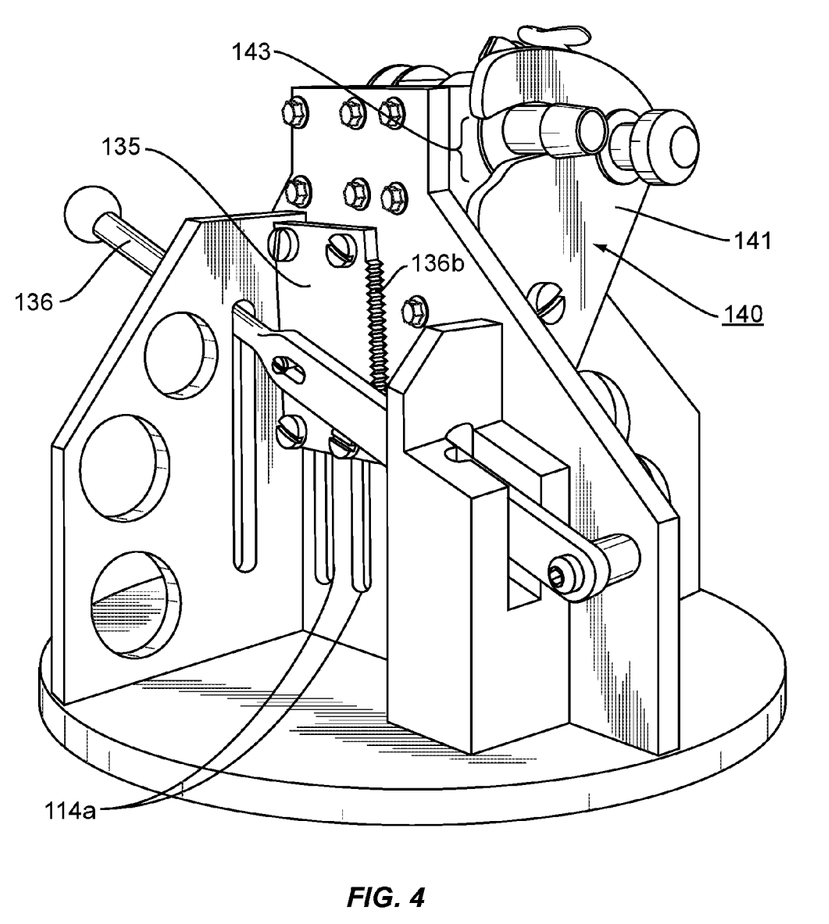
FIG. 4 is a rear perspective view of the device of the present invention.
Figure 5:
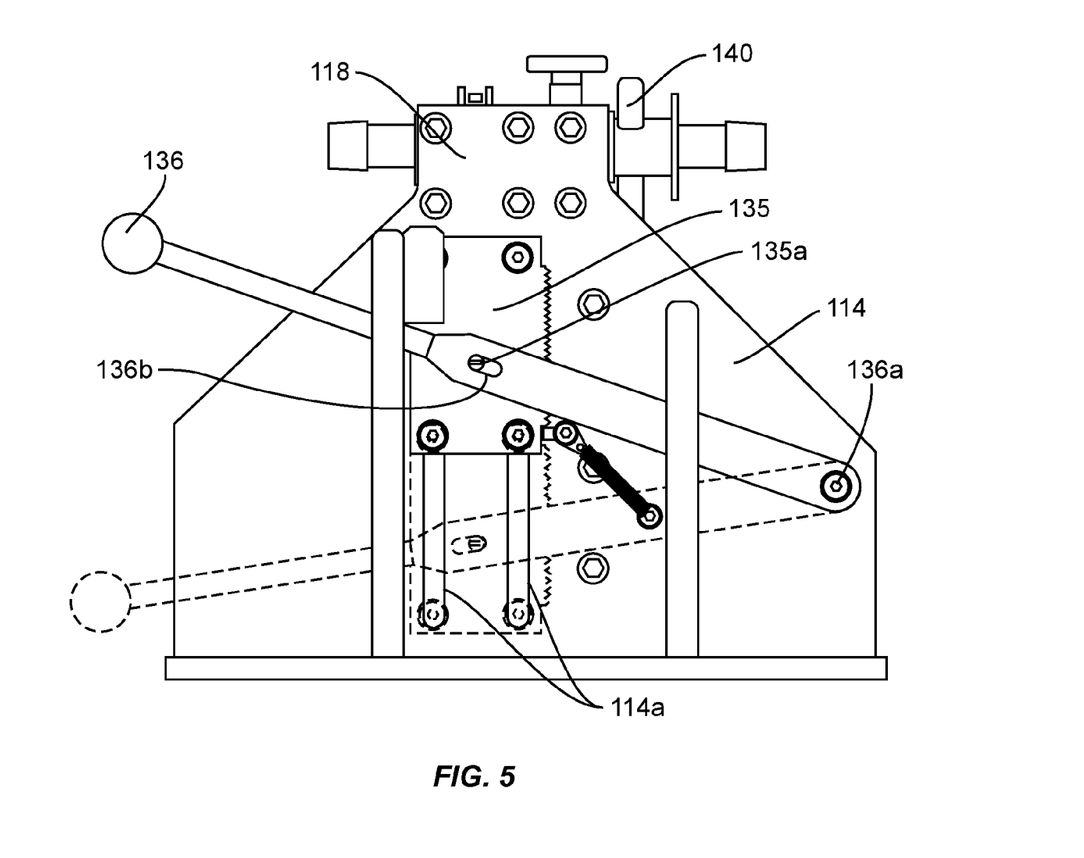
FIG. 5 is a rear elevational view of the device of the present invention.
Figure 6:
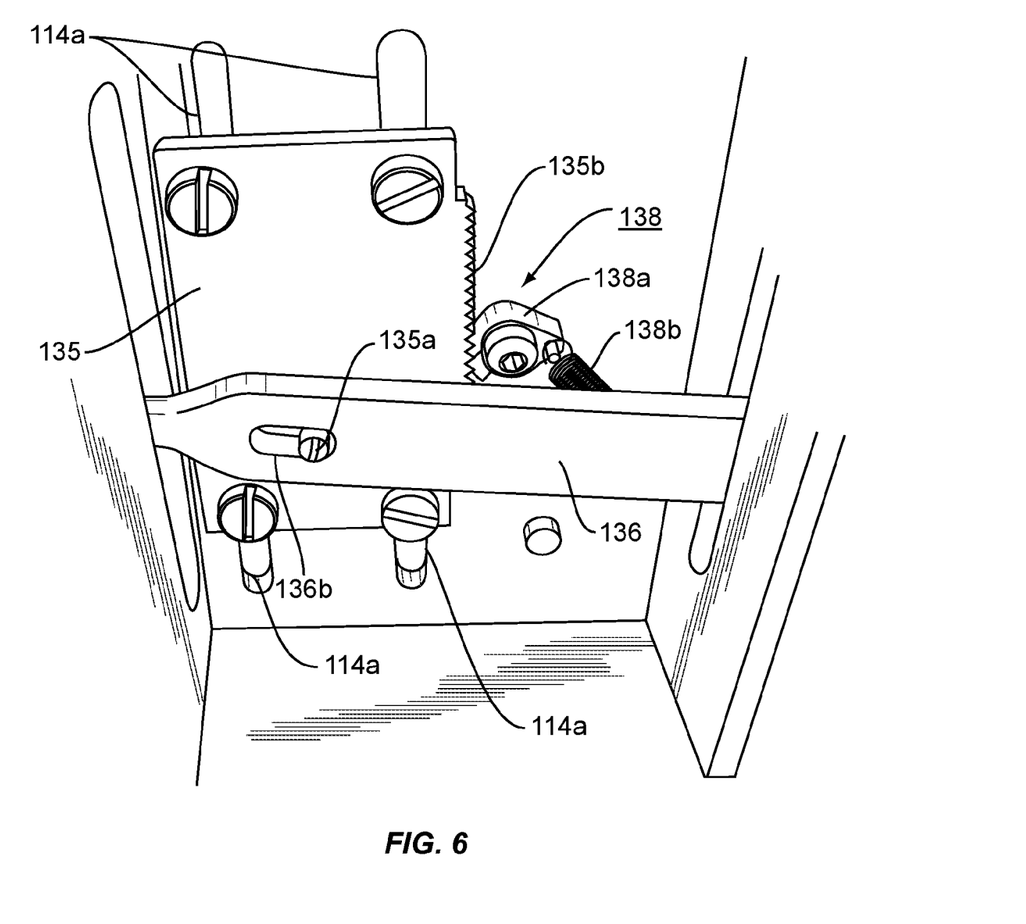
FIG. 6 is a close-up expanded view of the lever and ratchet assembly of FIG. 5.

Referring to FIGS. 3 and 4, with a connector 10 secured in the cradle 118, with the strips S extending downwardly through the slot 118a, the positive locking mechanism 133 is closed and locked in position, whereby the pair of strips S are positively held for subsequent withdrawal by the serrated teeth 132a, 134a. Turning to FIGS. 4 through 6, the back side of the strip removal assembly 130 is shown. A slidable rear mounting plate 135 is interconnected to the slidable front mounting plate 131 through the vertical slots 114a (see enlarged view in FIG. 6). A withdrawal lever 136 is mounted with one end 136a pivotally affixed to the rear of the wall 114. A guide pin 135a projects outwardly from the rear mounting plate 135 to engage an elongate slot 136b formed in the lever 136. The length of the slot 136b is sufficient to accommodate the movement of the pin 135a when the lever 136 is fully depressed downwardly to cause the strip withdrawal assembly 130 to simultaneously move downwardly, withdrawing the strips S.

As shown in FIG. 6, a ratchet mechanism 138, comprising a ratchet pawl 138a and a spring 138b, is configured to engage the serrated teeth 135b along the inner edge of the rear mounting plate 135. This is accomplished by the pivotal mounting of the ratchet pawl 138a, which is attached to the extension spring 138b. As the lever 136 is depressed downwardly, the rear mounting plate 135 slides downwardly in the vertical slots 114a, with the teeth 135b causing the ratchet pawl 138a to pivot downwardly. As will be appreciated, the spring 138b biases the ratchet pawl 138a upwardly against the teeth 135b so that the movement of the lever cannot be prematurely reversed to return to the "home" position until the complete downward withdrawal stroke is performed. Thus, with the toggle clamp assembly 133 in a closed position, operation of the lever 136 ensures that the vented peel-away strips S are both simultaneously withdrawn in a straight line pull.

Following withdrawal of the strips S, the user rotates the thumb rest 12a on the male portion 12 of the connector 10 one partial turn and pushes the male portion 12 into full engagement with the female portion 18. As best shown in FIGS. 2 and 4, the device 100 further comprises an engagement gauge 140. The engagement gauge 140 has an arm 141, which is pivotally mounted to a wall 116. A notch 143 is formed in one side of the arm 141, the notch 143 corresponding in dimension (diameter) to the diameter of the male portion 12; i.e., that diameter of the male portion 12 which mates with the tubing to form a fluid pathway. The engagement gauge 140 ensures that the male and female portions of the connector are fully engaged. If fully engaged, when the engagement gauge 140 is pivoted upwardly, it will engage the male portion 12 behind the flange 12b (see FIG. 1B). If the male and female portions are not fully engaged, then the engagement gauge 140 cannot engage the male portion 12.

Turning lastly to FIG. 7, in view of FIGS. 1A through 6, operation of the device is schematically illustrated. First (Step 1), the connector assembly (male and female portions) are placed in the cradle, with the vented strips S extending through the slot to position the strips S between the serrated teeth 132a, 134a. The positive locking mechanism 126 is then pivoted closed to secure the connector in place (Step 2). Pivotal toggle 135 is then closed, capturing the pair of vented strips S between the serrated teeth 132a 134a of the strip removal assembly 130 (Step 3). With the clamp portions engaged, the lever 136 is depressed downwardly (Step 4) to simultaneously pull the strips S downwardly from between the male 12 and female 18 portions of the connector. The connector is next actuated by manually twisting the thumbrest 12a of the male portion 12 a partial turn and pushing it fully into the female portion 18 (Step 5). Lastly, the engagement gauge 140 is pivoted upwardly into position to encompass the male portion flange 12a (Step 6). The engagement guide 140 will not move into position against the flange unless the connector portions are in 100 percent engagement.

The invention has been described herein in terms of several embodiments and constructions that are considered by the inventor to represent the best mode of carrying out the invention. It will be understood by those skilled in the art that various modifications, variations, changes and additions can be made to the illustrated embodiments without departing from the spirit and scope of the invention. These and other modifications are possible and within the scope of the invention as set forth in the claims.

I claim:

1. A device for ensuring the sterile integrity of two separate fluid pathways during interconnection of the two pathways with a two-part connector assembly comprising male and female portions, each portion initially having a port covered and protected by a peel-away strip, the device comprising:
   (a) a base assembly;
   (b) a connector clamp assembly mounted to the base assembly and configured for securing the two-part connector assembly in position during interconnection of the male and female portions; and
   (c) a strip withdrawal assembly mounted to the base assembly and configured for simultaneous withdrawal of the peel-away strips from the ports of the male and female portions.

2. The device of claim 1, wherein the base assembly comprises a base having at least one upstanding wall extending therefrom, the upstanding wall having a front surface and a rear surface.

3. The device of claim 2, further comprising a cradle affixed to the at least one upstanding wall and dimensioned for holding the two-part connector assembly.

4. The device of claim 3, wherein the cradle further comprises a slot for the peel-away strips of the male and female portions of the two-part connector assembly to extend therethrough.

5. The device of claim 3, wherein the connector clamp assembly comprises:
   (a) a mounting arm pivotally connected to the base; and
   (b) a toggle clamp connected to the mounting arm and comprising a positive locking mechanism,
   wherein the positive locking mechanism secures the two-part connector assembly in position when the mounting arm and connected toggle clamp are pivoted toward the cradle.

6. The device of claim 2, wherein the strip removal assembly comprises:
   (a) a first plate slideable adjacent the front surface of the at least one upstanding wall along vertical slots formed in the at least one upstanding wall, the first plate having an uppermost vertical position;
   (a) a first clamp portion affixed to the first plate and having a first clamping surface;
   (c) a second clamp portion pivotally connected to the first clamp portion and having a second clamping surface; and
   (d) a toggle clamp connected to the second clamp portion and comprising a positive locking mechanism, the toggle clamp having an open position and a closed position;
   wherein with the first plate in the uppermost vertical position, the second clamp portion pivoted toward the first clamp portion, and the toggle clamp secured in a closed position by the positive locking mechanism, the strip removal assembly will positively grip the peel-away strips covering the ports of the male and female portions of the two-part connector assembly.

7. The device of claim 6, wherein at least one of the first clamping surface of the first clamp portion and the second clamping surface of the second clamp portion comprises serrated teeth.

8. The device of claim 6, further comprising:
   (a) a second plate slideable adjacent the rear surface of the at least one upstanding wall along the vertical slots, the first plate having side edges and an uppermost vertical position in registration with the uppermost vertical position of the first plate; and
   (b) a lever comprising a first end pivotally connected to the at least one upstanding wall, a second free end, the lever slideably connected between the first end and second free end to the second plate, and having an uppermost position;
   wherein when the peel-away strips of the two-part connector assembly are positively gripped by the first and second clamp portions, and the lever is pivoted downwardly from the uppermost position, the peel-away strips are simultaneously withdrawn to uncover the ports of the male and female portions of the two-part connector assembly.

9. The device of claim 8, wherein the strip removal assembly further comprises:
   (a) a gripping surface on one of the side edges of the second plate, the gripping surface having an upper end and a lower end;
   (b) a ratchet mechanism for engaging the gripping surface to limit upward movement of the lever, and for disengaging the gripping surface when the lever is moved downwardly to permit downward movement of the lever.

10. The device of claim 9, wherein the ratchet mechanism comprises a pawl and a spring, and wherein the spring biases the pawl against the gripping surface.

11. The device of claim 2, further comprising an engagement guide, having:
   (a) an arm pivotally mounted to the at least one upstanding wall; and
   (b) a notch formed in the arm and extending inwardly from an outer edge of the arm, the notch dimensioned to fit around the male portion of the two-part connector assembly, ensuring proper engagement of the male and female portions of the two-part connector assembly following withdrawal of the peel-away strips.

* * * * *